(12) United States Patent
Salazar et al.

(10) Patent No.: US 9,144,388 B2
(45) Date of Patent: Sep. 29, 2015

(54) PORTABLE SYSTEM AND METHOD FOR MONITORING OF A HEART AND OTHER BODY FUNCTIONS

(71) Applicants: Alfred Salazar, Mission, TX (US); Hilary F. Almeida, McAllen, TX (US); Peter L. Dy, McAllen, TX (US); Alexandria Salazar, Tulsa, OK (US)

(72) Inventors: Alfred Salazar, Mission, TX (US); Hilary F. Almeida, McAllen, TX (US); Peter L. Dy, McAllen, TX (US); Alexandria Salazar, Tulsa, OK (US)

(73) Assignee: Alfred Salazar, Mission, TX (US)

( * ) Notice: Subject to any disclaimer, the term of this patent is extended or adjusted under 35 U.S.C. 154(b) by 0 days.

(21) Appl. No.: 13/920,137

(22) Filed: Jun. 18, 2013

(65) Prior Publication Data
US 2013/0345540 A1    Dec. 26, 2013

Related U.S. Application Data

(63) Continuation-in-part of application No. 12/320,151, filed on Jan. 20, 2009, now Pat. No. 8,467,860.

(51) Int. Cl.
*A61B 5/0404* (2006.01)
*A61B 5/0408* (2006.01)
(Continued)

(52) U.S. Cl.
CPC .............. *A61B 5/0404* (2013.01); *A61B 5/0006* (2013.01); *A61B 5/044* (2013.01);
(Continued)

(58) Field of Classification Search
CPC .. A61B 5/0402; A61B 5/0006; A61B 5/0245; A61B 5/053; A61B 5/02; A61B 5/0205; A61B 5/0422; A61B 5/04012; A61B 5/0478; A61B 5/0432; A61B 2560/0468; A61B 5/024; A61B 5/044; A61B 5/04085; A61B 5/0537; A61B 5/063; A61B 2562/0209; A61B 5/0404; A61B 5/0482; A61N 1/36585; A61N 1/36521; A61N 1/3702; A61N 1/365; A61N 1/37; A61N 1/36135; A61N 1/3756; A61N 1/3622; A61N 1/368; A61N 1/025; A61N 1/08; A61N 1/3686; A61M 2230/04; G06F 19/3406; G06F 19/3418
USPC .................. 600/301, 508–509, 513, 522–523
See application file for complete search history.

(56) References Cited

U.S. PATENT DOCUMENTS 5,511,553 A * 4/1996 Segalowitz .................... 600/508
7,277,752 B2  10/2007 Matos
(Continued)

FOREIGN PATENT DOCUMENTS

WO    WO 2012158190    11/2012
WO    WO 2013112979    8/2013
WO    WO 2014145927    9/2014

*Primary Examiner* — Deborah Malamud
(74) *Attorney, Agent, or Firm* — Lindauer Law, PLLC

(57) ABSTRACT

Portable systems and methods for obtaining an electrocardiogram reading include a portable device having first and second electrodes with differing impedances. Computer instructions instruct a processor of the portable device to output instructional information relating to placement of the electrodes, receive confirmation of the positioning, and calculate lead values using readings from the first electrode, the second electrode, or combinations thereof, such that multiple bipolar and precordial leads can be measured. Augmented leads can be extrapolated using a known geometric relationship and the bipolar lead measurements. An electrocardiogram reading can be calculated from the lead measurements, then output, stored, transmitted, or combinations thereof. An alert response can be generated if the electrocardiogram reading deviates from selected threshold parameters.

19 Claims, 2 Drawing Sheets

(51) Int. Cl.
*A61B 5/00* (2006.01)
*A61B 5/044* (2006.01)
*A61B 5/0432* (2006.01)
*A61B 5/04* (2006.01)
*A61B 5/0402* (2006.01)

(52) U.S. Cl.
CPC .......... *A61B 5/0432* (2013.01); *A61B 5/04085* (2013.01); *A61B 5/6804* (2013.01); *A61B 5/6898* (2013.01); *A61B 5/7405* (2013.01); *A61B 5/749* (2013.01); *A61B 5/04012* (2013.01); *A61B 5/04028* (2013.01)

(56) References Cited

U.S. PATENT DOCUMENTS

| | | | |
|---|---|---|---|
| 8,301,232 | B2 | 10/2012 | Albert et al. |
| 8,509,882 | B2 | 8/2013 | Albert et al. |
| 2007/0276270 | A1 | 11/2007 | Tran |
| 2011/0301439 | A1 | 12/2011 | Albert et al. |
| 2012/0172689 | A1 | 7/2012 | Albert et al. |
| 2013/0197320 | A1 | 8/2013 | Albert et al. |

* cited by examiner

PORTABLE SYSTEM AND METHOD FOR MONITORING OF A HEART AND OTHER BODY FUNCTIONS

CROSS-REFERENCE TO RELATED APPLICATIONS

The present application is a continuation-in-part application that claims priority to the U.S. application for patent having the Ser. No. 12/320,151, filed Jan. 20 2009, now issued as U.S. Pat. No. 8,467,860, which is incorporated by reference in its entirety herein.

FIELD

The present embodiments relate, generally, to portable systems and methods for monitoring of a user's heart activity, usable for medical evaluation, health awareness, emergency response, and/or other related purposes. Specific embodiments can include devices, methods, and systems for adapting a pre-existing portable device, such as a cellular telephone or portable computer, to acquire twelve-lead electrocardiograms and/or other usable data from an individual for storage and/or transmission, e.g., for immediate or future response and/or evaluation.

BACKGROUND

Conventional medical equipment for obtaining a complete, twelve-lead electrocardiogram reading from an individual is typically restricted to use in a hospital or other medical setting. Such equipment is normally bulky and requires use of at least nine wired electrodes, placed at precise locations on the individual's body, that communicate with a central processing machine, to obtain measurements used to construct the electrocardiogram. Such equipment has not been suitable for continuous monitoring of an individual or discrete instances of monitoring of an individual in a non-medical setting, as the equipment is not readily portable, and precise placement of electrodes (e.g., by trained medical personnel) is necessary to ensure the accuracy of the readings obtained.

Attempts have been made to create portable means for obtaining electrocardiogram readings, specifically useful for monitoring individuals with potential heart conditions outside of a medical facility. However, these portable devices are typically limited to two or three sensors, which measure heart rate, rhythm, and similar conditions, then construct an electrocardiogram waveform using artificial algorithmic modeling processes. Electrocardiograms obtained in this matter are not as accurate nor as complete as a twelve-lead electrocardiogram.

As such, a twelve-lead electrocardiogram is specifically intended for use as a diagnostic measurement, which can detect subtle conditions, among other uses. Electrocardiograms obtained using a reduced number of sensors and readings, and numerous mathematical extrapolations, do not obtain QRS-ST-T waveforms with complete accuracy and are typically useful only for determining cardiac rate and rhythm, and possibly the immediate presence of highly obvious symptoms, such as an emergent cardiac event that is currently occurring.

A need exists for a portable heart monitoring system usable to monitor the heart activity of a user in a continuous manner or through discrete instances, to obtain a complete, twelve-lead electrocardiogram reading, using existing portable devices commonly available to most users, such as cellular telephones or portable computers. Portable devices can conveniently be used to store, analyze, and/or transmit readings (e.g., for analysis by remote medical personnel).

A need also exists for a portable heart monitoring system that can be used to obtain an accurate, twelve-lead electrocardiogram reading by a user of the system (e.g., non-medical personnel) or by a third party in the presence of the user (e.g., if a user is physically or medically unable to make use of the system). A portable system able to continuously or discretely obtain a complete and accurate, twelve-lead electrocardiogram reading would be of significant benefit to individuals having suspected and/or potential heart conditions, which require that the individual be monitored over a lengthy period of time to diagnose the presence or absence of such conditions.

A further need exists for a portable heart monitoring system usable to continuously or periodically monitor a mobile user, such as during athletic events and other instances of physical activity, that can be accessible at any time to obtain the measured data in a variety of output formats.

A need also exists for a portable heart monitoring system that can coordinate data between a centralized database, medical facilities, physicians, insurance providers, and/or other similar individuals and organizations for streamlining the diagnosis, care, and treatment of an individual.

Additionally, a need exists for a portable heart monitoring system usable to detect a heart attack or similar emergency and trigger a response by recognizing a potential emergency condition that exceeds a predetermined safe threshold, and automatically and wirelessly contacting appropriate medical, insurance, and/or emergency response personnel for responding to the user at a specific location.

A further need exists for a portable heart monitoring system able to make electrocardiogram technology widely available for screening of a larger segment of the population (e.g., school-aged children) for potentially serious cardiac abnormalities, independent of the logistical and economic barriers that currently make widespread electrocardiogram screening economically unfeasible.

Embodiments usable within the scope of the present disclosure meet these needs.

SUMMARY

Embodiments usable within the scope of the present disclosure relate, generally, to systems and methods usable to monitor heart activity of a user. Such systems can include a portable device having a processor, data storage, a transmitter, an input device, and an output device. For example, a cellular telephone, a portable computer, or a similar portable device could be used in one or more embodiments. A cellular telephone, by way of example, includes a processor, data storage (integral (e.g., built-in), removable (e.g., an SD card or similar media), and/or remote (e.g., network-based and/or "cloud" storage)), one or more types of transmitters (cellular, Wi-Fi™, Bluetooth®, etc.), one or more types of input devices (touchscreen, keyboard, buttons, microphone, etc.), and one or more types of output devices (speakers, lights, display screen, etc.).

A first electrode can be positioned on a first portion of the portable device, while a second electrode is positioned on a second portion of the device, each electrode being usable to individually or simultaneously contact a user and receive signals therefrom. In an embodiment, a first electrode could be positioned on the back surface of a cellular telephone or similar device, while a second electrode is positioned on a side or front surface thereof, such that neither electrode interferes with the display, input, and/or output devices of the portable device, and while both electrodes can comfortably contact different portions of a user's body. While embodiments can include electrodes that are integral with and/or otherwise built into a portable device, other embodiments can include a case, cover, attachment, or other type of separate device having electrodes associated therewith, such that engagement of the case, cover, and/or attachment with the portable device enables transmission of information between the electrodes and the portable device.

The first and second electrodes can each be configured with a respective impedance, such as through a difference in size (e.g., the second electrode could be smaller than the first), introduction of a resistance in series with respect to the lesser electrode, or other means, such that when desired, the second electrode can selectively be caused to act as an indifferent electrode. For example, when measuring a bipolar lead, it is typically desirable to measure the difference across two electrodes that contact respective portions of a user's body; however, when measuring a precordial lead, it is normally desired to measure the reading obtained using a single electrode, while one or more other electrode(s) function as an indifferent electrode.

Computer instructions (e.g., software) in the data storage and/or otherwise accessible by the processor are usable to receive readings from the first and second electrodes, and calculate a lead value using the reading from one or both electrodes. As described above, calculation of a bipolar lead typically involves measuring the difference across two electrodes, while calculation of a precordial lead involves measuring a reading from a single electrode.

To facilitate proper positioning of the electrodes, computer instructions can further cause the processor to provide instructional information relating to the placement of the electrodes using the output device. By way of example, speakers on a cellular telephone, portable computer, or similar portable device can be used to provide audible instructions. Alternatively or additionally, a display screen can be used to provide visual instruction (e.g., a picture or video showing proper positioning of the electrodes.) In further embodiments, signals received from the electrodes can be compared with expected threshold values to determine proper positioning thereof, and/or tactile/positional sensors of the portable device could be used for such a purpose. The computer instructions can further enable receipt of confirmation from the input device to indicate that the portable device has been positioned. In an embodiment, the electrodes and/or similar detection components can have the ability to acquire readings from a plurality of locations on a user when placed at a single position, such that a plurality of bipolar and precordial leads can be acquired after positioning the portable device a single time.

One or more extrapolated leads can be calculated using the measured lead values. For example, augmented leads can be determined using measured bipolar leads and a known geometric algorithm/relationship. Alternatively, augmented leads can be calculated directly (e.g., using a first electrode as a positive electrode and one or more other electrodes as a negative electrode). The measured bipolar, precordial, and extrapolated leads can be used to calculate an electrocardiogram for storage (e.g., within the data storage of the portable device or remote therefrom) and/or transmission (e.g., to a medical facility or remote storage for immediate or future analysis). In an embodiment, the electrocardiogram can be output by the portable device. Measured parameters can be compared with standard and/or preselected values, such that deviation from standard values that exceeds a threshold can trigger an alert action. Alert actions can include visible, audible, and/or tactile indicia provided by the portable device, automatic transmission of data to remote facilities (e.g., medical facilities), automatic contact of emergency personnel, and/or other similar actions. The threshold parameters can be general, or specific to a user, depending on any known or suspected heart conditions or other medical conditions of the user. Customized threshold parameters specific to a patient can be provided and/or set by a physician, a technician, or another medical provider, and/or technologist.

Embodiments usable within the scope of the present disclosure can thereby incorporate use of a portable device having a processor, which eliminates the need for bulky and expensive medical monitoring and processing equipment, while simultaneously providing the user with the conventional telephone, e-mail, web browsing, Global Positioning System, text messaging, and music storage and playback capabilities of a typical portable (smart) telephone or computer. The built-in capabilities of such a portable device can also be used to locate a user (e.g., during an emergent situation), transmit and receive data, alerts, and other communications (e.g., via phone, e-mail, text message, etc.), and the like, which can streamline an emergency response, medical treatment, and/or insurance processing, while also facilitating the storage, processing, transmission, and maintenance of electrocardiogram-related data.

BRIEF DESCRIPTION OF THE DRAWINGS

In the detailed description of the embodiments presented below, reference is made to the accompanying drawings, in which.

Figure 1A:
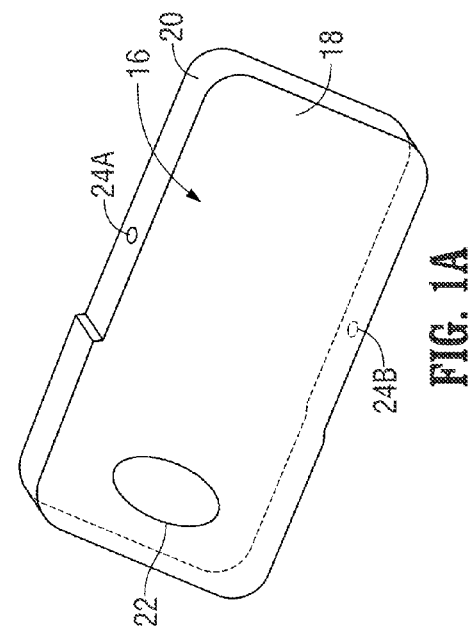
FIG. 1A depicts a rear view of an embodiment of a portable device usable within the scope of the present disclosure.

The present embodiments are detailed below with reference to the listed Figures.

DETAILED DESCRIPTION OF THE EMBODIMENTS

Before explaining the present embodiments in detail, it is to be understood that the embodiments are not limited to the particular descriptions and that the embodiments can be practiced or carried out in various ways.

An electrocardiogram is a measurement of a heart's electrical signal, depicted using P-QRS-T waveforms (which can be used to determine P-R and Q-T intervals and ST segments), which may be obtained by measuring the detected signal of the heart from a variety of angles. Conventional medical equipment used to obtain an electrocardiogram reading requires at least nine electrodes or similar sensors to be attached to a patient's limbs, and precisely positioned at six locations on a user's chest.

A complete electrocardiogram is formed by calculating twelve lead values. Three bipolar leads (Leads I, II, and III) are measured by calculating the difference in signal across two sensors, using both a positive and negative electrode. Lead I is typically determined through the difference in the readings obtained by electrodes on a patient's left arm and right arm. Lead II is typically determined through the difference in readings obtained by electrodes on the patient's left leg and right arm. Lead III is typically determined through the difference in the readings obtained by electrodes on the patient's left leg and left arm.

Three augmented voltage leads (Leads aVR, aVL, and aVF—which are abbreviations for augmented voltage right arm, left arm, and foot) are unipolar leads measured using a single electrode on a patient's limb as a positive electrode, and a ground electrode, termed the central terminal of Wilson, created using two other electrodes. The aVR lead is determined by using an electrode on the patient's right arm as a positive electrode, and those on the patient's left arm and left leg as negative electrodes. The aVL lead is determined by using an electrode on the patient's left arm as a positive electrode, and those on the patient's right arm and left leg as negative electrodes. The aVF lead is determined by using an electrode on the patient's left leg as a positive electrode, and those on the patient's right and left arms as negative electrodes. Because a known geometric relationship between the bipolar and augmented leads exists, it is possible to mathematically calculate the augmented lead values using the measured bipolar lead values, and/or to calculate the bipolar lead values using the measured augmented lead values.

Six precordial leads (termed V1 through V6) are positive unipolar leads, measured using single electrodes placed on a patient's chest. A first electrode is positioned to the right of the sternum, over the fourth intercostal space; a second electrode is positioned horizontally even with the first electrode, to the left of the user's sternum, over the fourth intercostal space; a third electrode is positioned below and to the right of the second electrode, over the fifth intercostal space; a fourth electrode is positioned at the midpoint between the second and third electrodes; a fifth electrode is positioned horizontally even with the third electrode, at the left anterior axillary line; and a sixth electrode is positioned horizontally even with the third and fifth electrodes, at the left midaxillary line underneath the patient's left arm. Each electrode obtains one of Leads V1 through V6. Leads V1 and V2 observe the right side of the heart, facing the user's back. Leads V3 and V4 observe the interventricular septum, facing the user's back. Leads V5 and V6 observe the left side of the heart, facing the user's back.

As such, the act of obtaining an electrocardiogram reading requires an abundance of equipment, which must be precisely positioned and utilized by trained medical personnel. While simpler alternatives have been attempted, the absence of precisely-positioned equipment by trained personnel requires numerous mathematical models and extrapolations to be used to calculate probable values for leads that are not measured, hindering the accuracy and utility of the data. Embodiments usable within the scope of the present disclosure relate to systems and methods that can be capable of acquiring an accurate electrocardiogram reading while reducing the equipment and training necessary to do so.

Figure 1B:
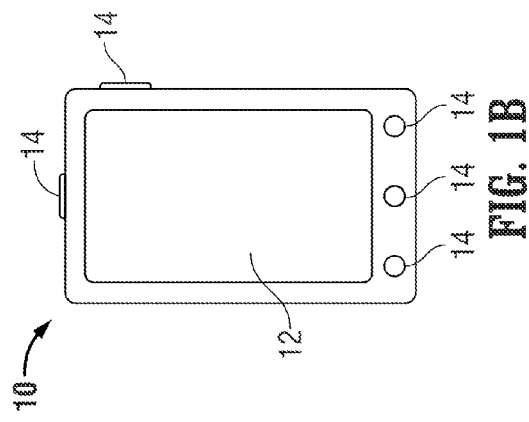
FIG. 1B depicts a front view of the portable device of FIG. 1A.

Referring now to FIGS. 1A and 1B, an embodiment of an exemplary device usable with embodiments of the present systems and methods is depicted. Specifically, FIG. 1B depicts a front view of the device, while FIG. 1A depicts a rear view thereof. The embodied device is illustrated as a cellular telephone (10); however, it should be understood that embodiments usable within the scope of the present disclosure can be used with any generally portable device (e.g., a handheld or portable computer, a laptop, or other similar devices) having a processor; integral, removable, and/or remote data storage; and some manner of integral, removable, and/or remote input and output devices. The illustrated cellular telephone (10) can include any manner of "smart" phone and is shown having a touch screen (12), which can function both as an output device (e.g., a display), and an input device, and a plurality of buttons (14), shown including physical and/or capacitive buttons on the front surface of the cellular telephone (10), and buttons (14) on the side and top surfaces thereof (e.g., volume controls, power buttons, etc.). Other type of phones, computers and/or similar devices, having keyboards, switches, and/or other types of input devices can also be used without departing from the scope of the present disclosure. The depicted cellular telephone (10) can also include a microphone and speakers (not visible in FIGS. 1A and 1B), usable as input and/or output devices (e.g., through use of speech recognition and/or delivery software, text-to-speech/speech-to-text programs, or other similar means).

The depicted cellular telephone (10) is further shown having a case and/or cover (16) secured over the rear and side surfaces thereof. The depicted case and/or cover (16) includes a first electrode (22) on the rear surface (18) thereof, and is also shown having two locations along the side surface (20) suitable for placement of a second electrode (24A, 24B). The first electrode (22) is shown being larger in size than either second electrode (24A, 24B), such that when used concurrently, the first and second electrodes will have a difference in impedance that selectively enables one of the electrodes to act as an indifferent electrode. In an embodiment, a difference in impedance between the first and second electrodes could be generated through other means, such as use of electrical resistance and/or other internal components. It should be understood that while FIG. 1A depicts a single first electrode (22), and two possible locations for second electrodes (24A, 24B), embodiments usable within the scope of the present disclosure can include only a single second electrode (24) or more than two second electrodes (24). Embodiments may also include more than one first electrode (22) without departing from the scope of the present disclosure. Additionally, while FIG. 1A depicts a case and/or cover (16) able to be engaged with a cellular telephone (10) in a manner that the electrodes (22, 24A, 24B) can communicate with the processor and/or other internal components of the cellular telephone (10) (e.g., through engagement with USB, micro-USB, SD and/or other ports of the cellular telephone (10), or comparable features in other types of devices), it should be understood that in various embodiments, the electrodes (22, 24A, 24B) could be integral with the cellular telephone (10) (e.g., built-in), or separately engagable with the cellular telephone (10) in the absence of a case and/or cover (16). Further, while FIG. 1A depicts a first electrode (22) on a back surface (18) of the cellular telephone (10), and one or more second electrodes (24A, 24B) on a side surface (20) thereof to facilitate contacting the first and second electrodes with respective parts of a user's body, this configuration and placement is merely exemplary, and any number of electrodes could be placed at any location on a portable device, as desired, without departing from the scope of the present disclosure.

Figure 2:
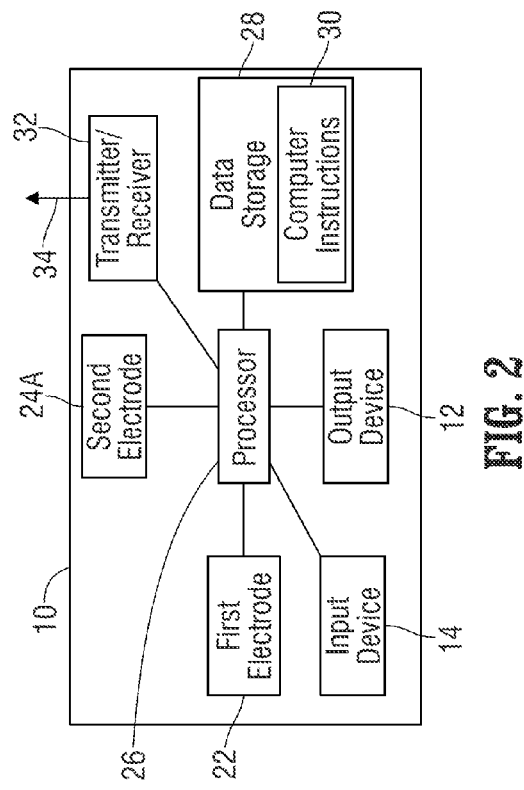
FIG. 2 depicts a diagram illustrating an embodiment of a configuration of components within the portable device of FIG. 1A.

Referring now to FIG. 2, a diagram illustrating an exemplary configuration of components within the cellular telephone (10) is depicted. The diagram shows a processor (26) in communication with the first and second electrodes (22, 24A), and the output and input devices (12, 14), described previously. It should be understood that while FIG. 2 labels the input device with the reference numeral 14, representative of the buttons depicted in FIG. 1B, the touch screen shown in FIG. 1B could function as both an input device or an output device. Similarly, as described above, the cellular telephone

(10) could include a microphone (not shown) usable as an input device and speakers (not shown) usable as an output device.

The processor (26) is further shown in communication with data storage (28) containing computer instructions (30) usable to instruct the processor (26) to perform various functions described above and below (e.g., receive data from the electrodes, store and retrieve data from the data storage, perform measurements, comparisons, analyses, communicate with the input and output devices, transmit and receive data using an associated transmitter, etc.). While FIG. 2 depicts the data storage (28) as fixed storage integrated within the cellular telephone (10), it should be understood that embodiments usable within the scope of the present disclosure could include removable data storage (e.g., SD cards, etc.) and/or remote data storage (e.g., network-based and/or "cloud" storage). A transmitter/receiver (32) is also shown in communication with the processor (26) and is usable to send signals (34) to remote storage, remote facilities for analysis, etc., and to receive signals (34) (e.g., alerts and information from remote facilities, output from remote processing of data, etc.).

The depicted portable device can be used to obtain an electrocardiogram reading through the following method, described below and illustrated in FIG. 3:

After initiating a program (e.g., an application or similar routine) to cause the processor (26) of the cellular telephone (10) to begin a series of steps to obtain an electrocardiogram reading, in Step 40, the output device (12) can be used to provide instructions to a user regarding placement of the electrodes (22, 24A). For example, using audio instructions provided through speakers of the cellular telephone (10) and/or a video illustration provided on the display screen (12), a user can be instructed to place the first electrode (22) into contact with the left arm and the second electrode (24A) into contact with the right arm. Typically, the cellular telephone (10) can be gripped such that the user's right thumb contacts the second electrode (24A), while the user's left thumb can be placed on the first electrode (22). In Step 42, the user can use the input device (14) (e.g., a button, a touch screen, or a vocal confirmation using a microphone (not shown) of the cellular telephone (10)) to confirm that the electrodes (22, 24A) have been properly positioned. After receiving confirmation from the user, in Step 44, the difference between electrodes (22, 24A) can be measured to obtain Lead I of an electrocardiogram reading. If the reading obtained from the electrodes (22, 24A) indicates that the electrodes (22, 24A) are not properly positioned, Steps 40 and 42 can be repeated.

In a similar manner, in Step 46, the output device (12) can be used to provide instructions to a user regarding placement of the electrodes (22, 24A) suitable to acquire a second bipolar lead. For example, using audio and/or video instructions, a user can be instructed to move the cellular telephone (10) such that the first electrode (22) contacts the user's left leg (e.g., the thigh thereof), while the right arm (e.g., the thumb thereof) remains in contact with the second electrode (24A). In Step 48, confirmation from the user that the electrodes have been positioned can be provided using the input device (14). In Step 50, the difference between electrodes (22, 24A) can be measured to obtain Lead II of the electrocardiogram reading.

In Step 52, the output device (12) can be used to provide instructions to a user regarding placement of the electrodes (22, 24A) suitable to acquire a third bipolar lead. For example, using audio and/or video instructions, a user can be instructed to move the cellular telephone (10) such that the first electrode (22) contacts the user's left leg (e.g., the thigh thereof), while the left arm (e.g., the thumb thereof) is placed in contact with the second electrode (24A). In Step 54, confirmation from the user that the electrodes have been positioned can be provided using the input device (14). In Step 56, the difference between electrodes (22, 24A) can be measured to obtain Lead III of the electrocardiogram reading.

In Step 58, the output device (12) can be used to provide instructions to a user regarding placement of the first electrode (22) suitable to acquire a first precordial lead. For example, using audio and/or video instructions, a user can be instructed to move the cellular telephone (10) such that the first electrode (22) contacts the appropriate location along the precordium for measuring Lead V1. In Step 60, confirmation from the user that the first electrode (22) has been positioned can be provided using the input device (14). In Step 62, the reading from the first electrode (22) can be measured to obtain Lead V1 of the electrocardiogram reading. During this measurement, the difference in impedance between the first and second electrodes can cause the second electrode (24A) to act as an indifferent electrode.

In Steps 64, 70, 76, 82, and 88, the output device (12) can be used to provide instructions to a user regarding placement of the first electrode (22) suitable to acquire the reaming five precordial leads (Leads V2 through V6). For example, using audio and/or video instructions, a user can be instructed to move the cellular telephone (10) such that the first electrode (22) contacts the appropriate location along the precordium for measuring Leads V2 through V6, respectively. In Steps 66, 72, 78, 84, and 90, confirmation from the user that the first electrode (22) has been positioned can be provided using the input device (14). In Steps 68, 74, 80, 86, and 92, the reading from the first electrode (22) can be measured to obtain Leads V2 through V6, respectively, of the electrocardiogram reading. During these measurements, the difference in impedance between the first and second electrodes (22, 24A) can cause the second electrode (24A) to act as an indifferent electrode.

In an embodiment, the measurement of leads V1 through V6 can include recording heart sounds of the user, e.g., using the microphone and/or other input devices of the cellular telephone (10), and/or using the first electrode (22) and/or other electrodes (e.g., the second electrode (24A) and/or other additional electrodes engaged with the portable device), through placement thereof into contact with the user's chest and/or in close proximity thereto, such that heart sounds can be detected and recorded. Detected heart sounds can be stored on the portable device, transmitted for analysis and/or storage, etc. Incorporation of heart sounds can provide additional information beyond what could normally be discovered through an electrocardiogram reading alone, such as the detection of pericardial friction, a systolic ejection murmur, aortic steonsis, or similar conditions that can be detected through analysis of heart sounds, especially when analyzed concurrently with an electrocardiogram reading.

Figure 4:
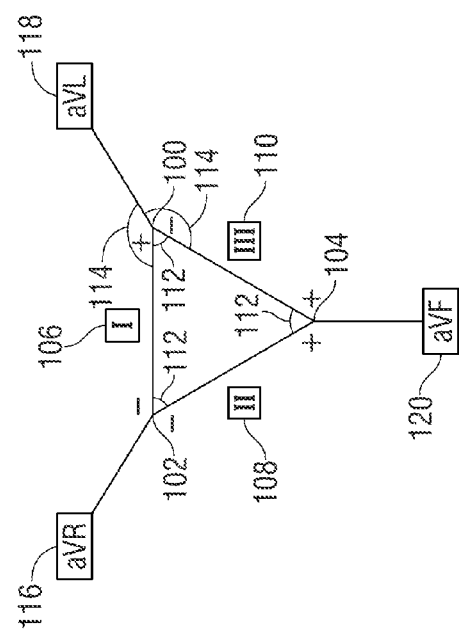
FIG. 4 depicts a geometric relationship between bipolar and augmented leads of an electrocardiogram.

In Step 94, the processor (26) can be used to calculate a plurality of extrapolated leads (e.g., the augmented leads aVR, aVL, and aVF) using a known geometric relationship between the bipolar leads (Leads I, II, and III) and the augmented leads. For example, FIG. 4 depicts the geometric relationship between the bipolar leads—Lead I (106), Lead II (108), and Lead III (110)—and the augmented leads—Lead aVR (116), Lead aVL (118), and Lead aVF (120). Reference point (100) represents an electrode placed in contact with a user's left arm, reference point (102) represents an electrode placed in contact with a user's right arm, and reference point (104) represents an electrode placed in contact with a user's leg.

To acquire a reading for Lead I (106), an electrode represented by reference point (100) is used as a positive electrode, while an electrode represented by reference point (102) is used as a negative electrode. To acquire a reading for Lead II (108), an electrode represented by reference point (104) is used as a positive electrode, while the electrode represented by reference point (102) is used as a negative electrode. To acquire a reading for Lead III (110), the electrode represented by reference point (104) is used as a positive electrode, while the electrode represented by reference point (100) is used as a negative electrode. The positioning of the electrodes represented by the reference points (100, 102, 104) and acquisition of the bipolar leads (106, 108, 110) defines an equilateral triangle having internal angles (112) of approximately sixty degrees. Thus, each of the augmented leads (116, 118, 120), which could normally be measured using one electrode as a positive electrode while the other two electrodes are negative electrodes, can also be calculated mathematically, since the exterior angles (114) defined between the augmented leads and the bipolar leads are known to have a measurement of 150 degrees. Therefore, in Step 94, a known algorithm can be applied by the processor (26) to compute three augmented lead values (aVR, aVL, and aVF) using the three bipolar lead values (I, II, and III).

In Step 96, each of the measured bipolar leads, precordial leads, and augmented leads can be used to calculate an electrocardiogram reading. In Step 98, the electrocardiogram reading can be output (e.g., using the display screen), stored in the data storage of the portable device, transmitted to a remote location (e.g., a medical facility for immediate or future analysis), or any combinations thereof. Optionally, in Step 99, the measured electrocardiogram reading can be compared with one or more threshold parameters to determine whether any deviations or factors exist that would cause an alert to be generated. Alert actions can include visible, audible, and/or tactile indicators provided by the portable device and/or at a remote location, an immediate analysis of the electrocardiogram reading by remote medical personnel, the automatic contact of emergency response personnel (e.g., using location features of the portable device, such as GPS or cellular signals, to direct the emergency personnel to the user), the automatic contact of family members and/or medical personnel, and/or other similar appropriate responses.

Figure 3:
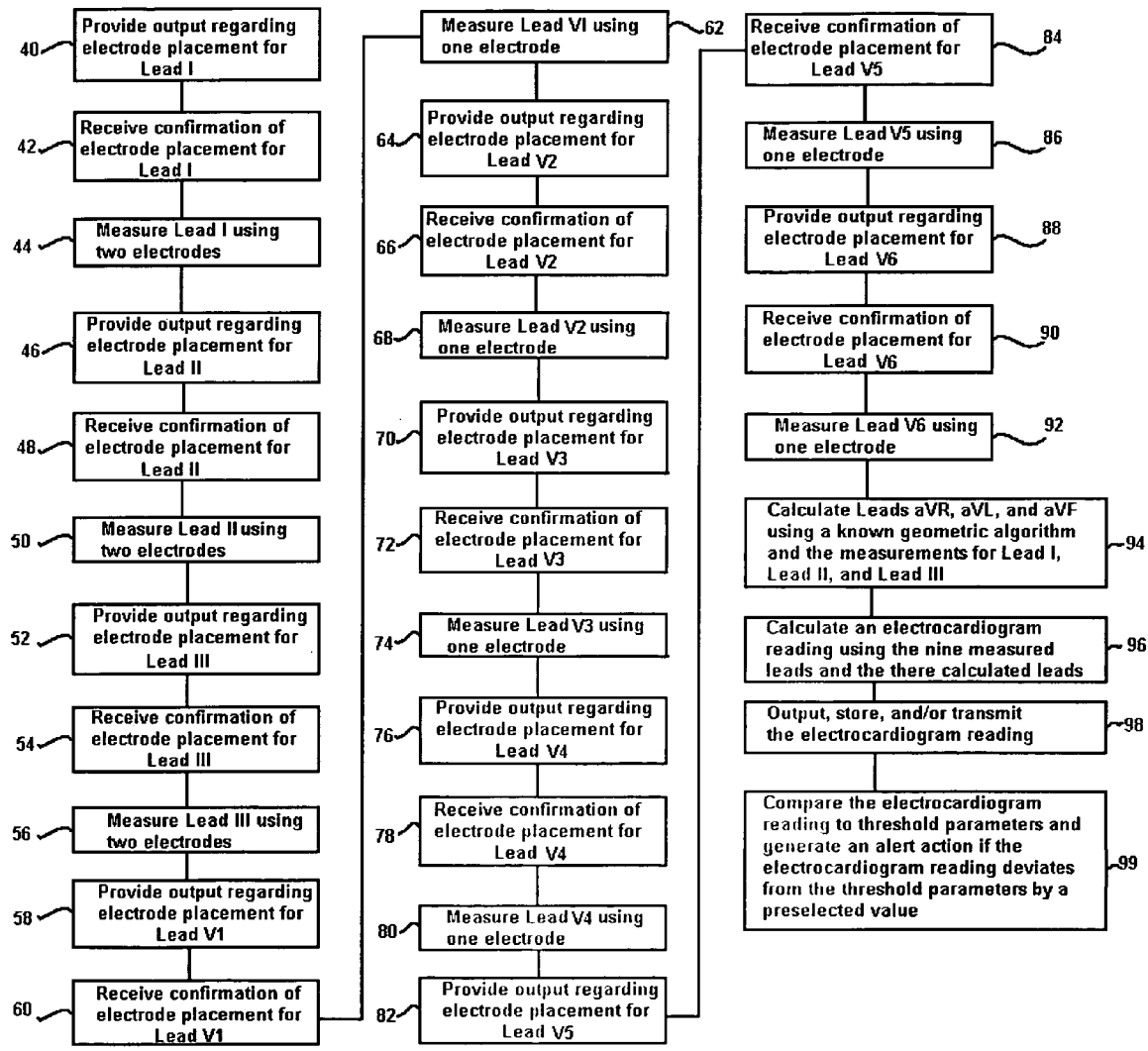
FIG. 3 depicts an embodiment of a method usable within the scope of the present disclosure.

While FIG. 3 illustrates one exemplary method by which a portable device can be used to acquire an electrocardiogram reading, it should be understood that technological capabilities of the portable device, the electrodes, the software, the transmitter/receiver, and/or other features described herein can enable other embodied methods to be practiced. For example, in an embodiment, electrodes that are able to obtain measurements without directly contacting a user can be used. In such embodiments, an electrode could be placed in a single location proximate to a user's chest, such that the electrode could acquire information sufficient to determine multiple precordial leads, and in an embodiment, all six precordial leads (Leads V1 through V6). As such, all of Steps 58 through 92, shown in FIG. 3, could be performed using only three steps: providing output regarding positioning of the first electrode; receiving input confirming positioning thereof; and measuring each of Leads V1 through V6 using the first electrode. In a similar manner, an electrode could be placed in a single location such that the electrode could acquire information sufficient to determine multiple precordial and/or bipolar leads. In other embodiments, an electrode could acquire multiple leads in a single step, e.g., as it is moved across a user's chest. In such embodiments, it may be unnecessary to provide instruction to a user and receive user confirmation before recording each lead measurement, as in an embodiment, a user could position the portable device once and provide a confirmation that the device has been positioned, then the device could acquire multiple leads.

Embodiments usable within the scope of the present disclosure can thereby incorporate use of a portable device that is usable to obtain a twelve-lead electrocardiogram reading, thereby eliminating the need for bulky and expensive medical monitoring and processing equipment by taking advantage of the processing, transmitting, storage, and input/output capabilities of an existing cellular telephone, portable computer, or similar device. Embodiments can further enable a method that can be performed easily by a single individual, to obtain an electrocardiogram for that individual, or by a third party in the event that an individual is incapacitated or otherwise unable to properly position the portable device. Embodiments can also incorporate use of sensors that may not require contact with a user's body, and/or that can acquire multiple lead values from a single position, thereby increasing the ease and efficiency of the process.

While certain embodiments have been described with emphasis, it should be understood that within the scope of the appended claims, the embodiments might be practiced other than as specifically described herein.

What is claimed is:

1. A portable system for monitoring heart activity of a user, the system comprising:
   a portable device comprising a processor, data storage, a transmitter, an input device, and an output device;
   a first electrode positioned on a first portion of the portable device, wherein the first electrode comprises a first impedance;
   a second electrode positioned on a second portion of the portable device, wherein the second electrode comprises a second impedance configured to cause the second electrode to selectively perform as an indifferent electrode and one or more of a positive electrode or a negative electrode;
   non-transitory computer instructions for instructing the processor to receive a reading from the first electrode, receive a reading from the second electrode, calculate a lead value using the reading from the first electrode, the reading from the second electrode, or combinations thereof, and store the lead value;
   non-transitory computer instructions for providing instructional information relating to positioning of the first electrode and the second electrode using the output device and receiving confirmation of the positioning of the first electrode and the second electrode from the input device;
   non-transitory computer instructions for calculating at least one extrapolated lead using a plurality of stored lead values;
   non-transitory computer instructions for calculating an electrocardiogram using the plurality of stored lead values and the at least one extrapolated lead for storage, transmission, or combinations thereof, transmitting the plurality of stored lead values and the at least one extrapolated lead for calculation of the electrocardiogram, or combinations thereof; and
   non-transitory computer instructions for outputting the electrocardiogram, information relating to the electrocardiogram, or combinations thereof using the output device.

2. The system of claim 1, wherein the portable device comprises a cellular telephone.

3. The system of claim 2, further comprising a case secured over the cellular telephone, wherein the case comprises a front side, a back side, and a side surface, and wherein the first electrode is positioned on the back side and the second electrode is positioned on the side surface or the front side.

4. The system of claim 1, wherein a difference between the first impedance and the second impedance is configured to cause the second electrode to act as an indifferent electrode when the first electrode is placed in contact with a precordial site on a user.

5. The system of claim 4, wherein the second electrode is smaller than the first electrode, thereby creating the difference between the first impedance and the second impedance.

6. The system of claim 4, wherein the second electrode comprises an electrical resistance greater than that of the first electrode, thereby creating the difference between the first impedance and the second impedance.

7. The system of claim 1, wherein the non-transitory computer instructions for instructing the processor to calculate the lead value using the reading from the first electrode, the reading from the second electrode, or combinations thereof instruct the processor to calculate a first bipolar lead, a second bipolar lead, and a third bipolar lead by measuring a difference between the reading from the first electrode and the reading from the second electrode to form the plurality of stored lead values while the second electrode functions as the one or more of the positive electrode or the negative electrode.

8. The system of claim 7, wherein the non-transitory computer instructions for instructing the processor to calculate the lead value using the reading from the first electrode, the reading from the second electrode, or combinations thereof further instruct the processor to calculate a first precordial lead, a second precordial lead, a third precordial lead, a fourth precordial lead, a fifth precordial lead, and a sixth precordial lead, using the reading from the first electrode while the second electrode functions as the indifferent electrode.

9. The system of claim 7, wherein the non-transitory computer instructions for calculating the at least one extrapolated lead using the plurality of stored lead values instruct the processor to calculate a first augmented lead, a second augmented lead, and a third augmented lead using a known geometric algorithm, the first bipolar lead, the second bipolar lead, and the third bipolar lead.

10. The system of claim 1, wherein the output device comprises a speaker and a display screen, and wherein the non-transitory computer instructions for providing the instructional information using the output device instruct the processor to output audio instruction regarding placement of the first electrode and the second electrode using the speaker and a visual illustration regarding placement of the first electrode and the second electrode using the display screen.

11. The system of claim 1, wherein the input device comprises a microphone, the system further comprising non-transitory computer instructions for instructing the processor to receive heart sounds using the microphone, record the heart sounds, and store the recorded heart sounds in association with the electrocardiogram.

12. A portable system comprising:
a housing having a first side and a second side;
a first electrode positioned on the first side;
a second electrode positioned on the second side wherein the first electrode comprises a first impedance, and wherein the second electrode comprises a second impedance configured to cause the second electrode to selectively perform as an indifferent electrode and one or more of a positive electrode or a negative electrode;
a processor;
an output device; and
data storage comprising non-transitory computer instructions that when executed cause the processor to:
receive readings from one or more of the first electrode or the second electrode;
determine an electrocardiogram using the readings; and
output the electrocardiogram using the output device.

13. The system of claim 12, wherein the first side is positioned opposite the second side.

14. The system of claim 12, wherein the first side is positioned at a non-parallel angle relative to the second side.

15. The system of claim 12, further comprising:
a microphone; and
non-transitory computer instructions that when executed cause the processor to:
receive heart sounds using the microphone; and
one or more of: output the heart sounds using the output device or store the heart sounds in association with the electrocardiogram.

16. The system of claim 12, further comprising:
non-transitory computer instructions that when executed cause the processor to:
provide instructional information relating to positioning of the first electrode and the second electrode using the output device.

17. The system of claim 16, further comprising:
an input device; and
non-transitory computer instructions that when executed cause the processor to:
receive confirmation of the positioning of the first electrode and the second electrode from the input device.

18. A portable system comprising:
a first electrode comprising a first impedance;
a second electrode comprising a second impedance configured to cause the second electrode to selectively perform as an indifferent electrode and one or more of a positive electrode or a negative electrode;
a processor; and
data storage comprising non-transitory computer instructions that when executed cause the processor to:
calculate a first lead value from a first reading from the first electrode and a second reading from the second electrode while the second electrode functions as the one or more of the positive electrode or the negative electrode;
calculate a second lead value from a third reading of the first electrode while the second electrode functions as the indifferent electrode; and
determine an electrocardiogram based at least partially on one or more of the first lead value and the second lead value.

19. The system of claim 18, further comprising a case configured for securing to a portable device, wherein the case comprises a front side, a back side, and a side surface, and wherein the first electrode is positioned on the back side and the second electrode is positioned on the side surface or the front side.

* * * * *